(12) United States Patent
Okuno

(10) Patent No.: US 9,050,023 B2
(45) Date of Patent: Jun. 9, 2015

(54) X-RAY APPARATUS

(75) Inventor: Tomoharu Okuno, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 260 days.

(21) Appl. No.: 13/642,750

(22) PCT Filed: Mar. 7, 2011

(86) PCT No.: PCT/JP2011/001328
§ 371 (c)(1),
(2), (4) Date: Oct. 22, 2012

(87) PCT Pub. No.: WO2011/132359
PCT Pub. Date: Oct. 27, 2011

(65) Prior Publication Data
US 2013/0039465 A1    Feb. 14, 2013

(30) Foreign Application Priority Data

Apr. 20, 2010 (JP) ................................ 2010-097003

(51) Int. Cl.
*A61B 6/08* (2006.01)
*A61B 6/00* (2006.01)

(52) U.S. Cl.
CPC .............. *A61B 6/08* (2013.01); *A61B 6/4464* (2013.01); *A61B 6/4452* (2013.01); *A61B 6/5241* (2013.01); *A61B 6/547* (2013.01)

(58) Field of Classification Search
CPC ........ A61B 6/5241; A61B 6/08; A61B 6/544; A61B 6/545
USPC ................................. 378/205, 206
See application file for complete search history.

(56) References Cited

U.S. PATENT DOCUMENTS

| | | | | |
|---|---|---|---|---|
| 4,502,147 A | * | 2/1985 | Michaels | 378/206 |
| 7,114,849 B2 | * | 10/2006 | Atzinger et al. | 378/206 |
| 7,543,988 B2 | * | 6/2009 | Ramsauer | 378/206 |
| 7,555,100 B2 | * | 6/2009 | Wang et al. | 378/98.12 |
| 7,559,693 B2 | * | 7/2009 | Sonani | 378/206 |
| 8,011,829 B2 | * | 9/2011 | Sung et al. | 378/207 |
| 8,351,568 B2 | * | 1/2013 | Minnigh et al. | 378/62 |

(Continued)

FOREIGN PATENT DOCUMENTS

| | | |
|---|---|---|
| JP | 2004-358254 A | 12/2004 |
| JP | 2007-135692 A | 6/2007 |

(Continued)

OTHER PUBLICATIONS

International Search Report issued in International Patent Application No. PCT/JP2011/001328 dated May 31, 2011.

*Primary Examiner* — Michael Maskell
(74) *Attorney, Agent, or Firm* — McDermott Will & Emery LLP

(57) ABSTRACT

A controller determines a lower edge position of an imaging area of an image combined in long-length imaging through light illumination from a line marker. Thereby the controller performs control such that light from the line marker is switched off beyond an area, set in advance, capable of being imaged upon determination of the imaging area. Consequently, an operator just performs operation while looking at only light from the line marker upon determination of the imaging area, which achieves easy operation. As a result, operation upon determination of the imaging area can be facilitated.

20 Claims, 8 Drawing Sheets

(56) References Cited

U.S. PATENT DOCUMENTS

| | | | |
|---|---|---|---|
| 2004/0247081 A1* | 12/2004 | Halsmer et al. | 378/108 |
| 2007/0139799 A1* | 6/2007 | Ramsauer | 359/837 |
| 2009/0245464 A1* | 10/2009 | Yamaguchi | 378/62 |
| 2009/0257561 A1 | 10/2009 | Okuno et al. | |
| 2011/0064193 A1* | 3/2011 | Minnigh et al. | 378/62 |

FOREIGN PATENT DOCUMENTS

| | | |
|---|---|---|
| JP | 2007-185209 A | 7/2007 |
| JP | 2008-125981 A | 6/2008 |

* cited by examiner

X-RAY APPARATUS

CROSS REFERENCE TO RELATED APPLICATIONS

This application is the U.S. National Stage under 35 U.S.C. §371 of International Application No. PCT/JP2011/001328, filed on Mar. 7, 2011, which as published as WO 2011/132359 on Oct. 27, 2011. The application is incorporated herein by reference.

TECHNICAL FIELD

This invention relates to an X-ray apparatus for conducting X-ray radiography. Particularly, this invention is directed to a technique of combining two or more X-ray images.

BACKGROUND

Conventionally in such apparatus, an imaging distance of an X-ray tube (an X-ray irradiating device) to a subject is fixed. An X-ray detector (an X-ray detecting device) is then moved for every exposure in consideration of overlap of an exposure area from the X-ray tube in every sheet and a position of the X-ray detector within a long-length imaging area. See, for example, Japanese Patent Publications No. JP-A-2004-358254, JP-A-2007-135692, and JP-A-2007-185209.

In this case, examples of an imaging method includes a method of moving a focusing position of the X-ray tube parallel to the X-ray detector for every exposure as described in the prior art of JP-A-2007-135692 and in JP-A-2007-185209. Moreover, the examples include a method of varying an exposure angle of the X-ray tube for every exposure such that X-rays enter into the X-ray detector with a focusing position of the X-ray tube being fixed as described in JP-A-2004-358254 and JP-A-2007-135692. Subsequently, two or more successive X-ray images obtained for every exposure are combined in a direction of movement, whereby an X-ray image with a long area (long X-ray image) can be obtained.

Such approach as shown in FIG. 12 is conducted for determination of the long-length imaging area. As shown in FIG. 12, an X-ray tube 102 with a line marker 101 attached thereto as an illumination device is moved into a given position to determine an imaging distance D between the X-ray tube 102 and a subject M. Subsequently, the X-ray tube 102 is inclined with a focus of the X-ray tube 102 being fixed at the position, whereby the line marker 101 is also inclined. The X-ray tube 102 is inclined and an upper edge or a lower edge of the imaging area is illuminated by the line marker 101. Thereafter, a positioning button (e.g., a button on a touch panel attached to the X-ray tube 102) is depressed, whereby each position corresponding to the upper and lower edges is determined. The imaging area L can be determined geometrically from the determined imaging distance D and angles α, β of the X-ray tube 102 upon illuminating the upper and lower edges. In order to obtain a practical X-ray image, an X-ray detector 103 is moved such that X-rays enter into the X-ray detector 103.

Upon conducting radiography for obtaining a practical X-ray image, the imaging distance D and the imaging area L are determined. Then the X-ray tube 102 is inclined by an operator through depressing the exposure button by an operator, and the X-ray detector 103 is moved into a first exposure position such that X-rays emitted from the inclined X-ray tube 102 enter. Thereby radiography can be conducted. When radiography of a first X-ray image obtained in the first exposure position is completed, the X-ray tube 102 is inclined and the X-ray detector 103 is moved into a second exposure position. Likewise, radiography for obtaining X-ray images is repeated through inclination of the X-ray tube 102 and movement of the X-ray detector 103 until the number of images can be obtained with which the long-length imaging area can be covered. Here, the adjacent X-ray images overlap partially when combining them.

The movable area of the X-ray tube 102 or the X-ray detector 103 is restricted mechanically. For instance, when X-ray radiography is conducted while the subject is in a standing posture, the X-ray detector 103 is held on an erect stand while the movable area thereof is restricted through strut stroke of the erect stand. Consequently, the long-length imaging area is also restricted. Thus in order to obtain an area for the long imaging area where radiography is possible in determining the imaging area for the long-length imaging mentioned previously, notification is provided to the operator by changing display of the foregoing positioning button, for example, when the position of the upper edge or the lower edge is determined. Specifically, notification is provided to the operator by changing a color of the button into a background color of the foregoing touch pane to be undisplayed or by changing a shape of the button.

The conventional apparatus with such construction has the following drawback. Specifically, the upper edge and the lower edge of the long-length imaging area can be determined with the simple operation mentioned previously. On the other hand, upon determination of the upper and lower edges, operation should be performed while paying simultaneous attention to light from the illumination device toward the subject and the shape of the foregoing positioning button. Consequently, actual operation becomes extremely complicated. Such drawback may arise.

This invention has been made regarding the state of the art noted above, and its object is to provide an X-ray apparatus that can facilitate operation upon determination of an imaging area.

SUMMARY

This invention is configured as under to achieve the above object.

An X-ray apparatus for conducting X-ray radiography according to one example of this invention includes an X-ray irradiating device for irradiating a subject with X-rays, an X-ray detecting device for detecting X-rays transmitting through the subject, an image combining device for combining two or more X-ray images, a light illuminating device for illuminating light to the subject, an edge determining device for determining an edge of an imaging area of an image combined by the image combining device through light illumination by the light illuminating device, and a control device for performing control such that light from the light illuminating device is not emitted outside beyond an area, set in advance, capable of being imaged.

OPERATION AND EFFECT

According the X-ray apparatus in this example of the invention, the edge determining device determines an edge of an imaging area of the image combined by the image combining device through light illumination by the light illuminating device. Thereby the control device performs control such that light from the light illuminating device is not emitted outside beyond the area, set in advance, capable of being imaged upon determination of the imaging area. Consequently, an operator just performs operation while looking at only light from the light illuminating device upon determination of the imaging area, which achieves easy operation. As a result, operation upon determination of the imaging area can be facilitated.

The area capable of being imaged may be set in accordance with a movable area of the X-ray irradiating device, or may be set in accordance with an exposure area of the X-ray irradiating device. Alternatively, the area capable of being imaged may be set in accordance with a movable area of the X-ray detecting device. The area capable of being imaged may be set in accordance with such mechanical restrictions, and may be used for control of light illumination.

Control such that light from the light illuminating device is not emitted outside beyond the area, set in advance, capable of being imaged may be achieved through switching off the light illuminating device, or intercepting light by an intercepting device provided for intercepting light from the light illuminating device.

According to the X-ray apparatus in this example of the invention, the control device performs control such that light from the light illuminating device is not emitted outside beyond the area, set in advance, capable of being imaged. Consequently, an operator just performs operation while looking at only light from the light illuminating device upon determination of the imaging area. As a result, operation upon determination of the imaging area can be facilitated.

DESCRIPTION OF REFERENCES

Figure 1:
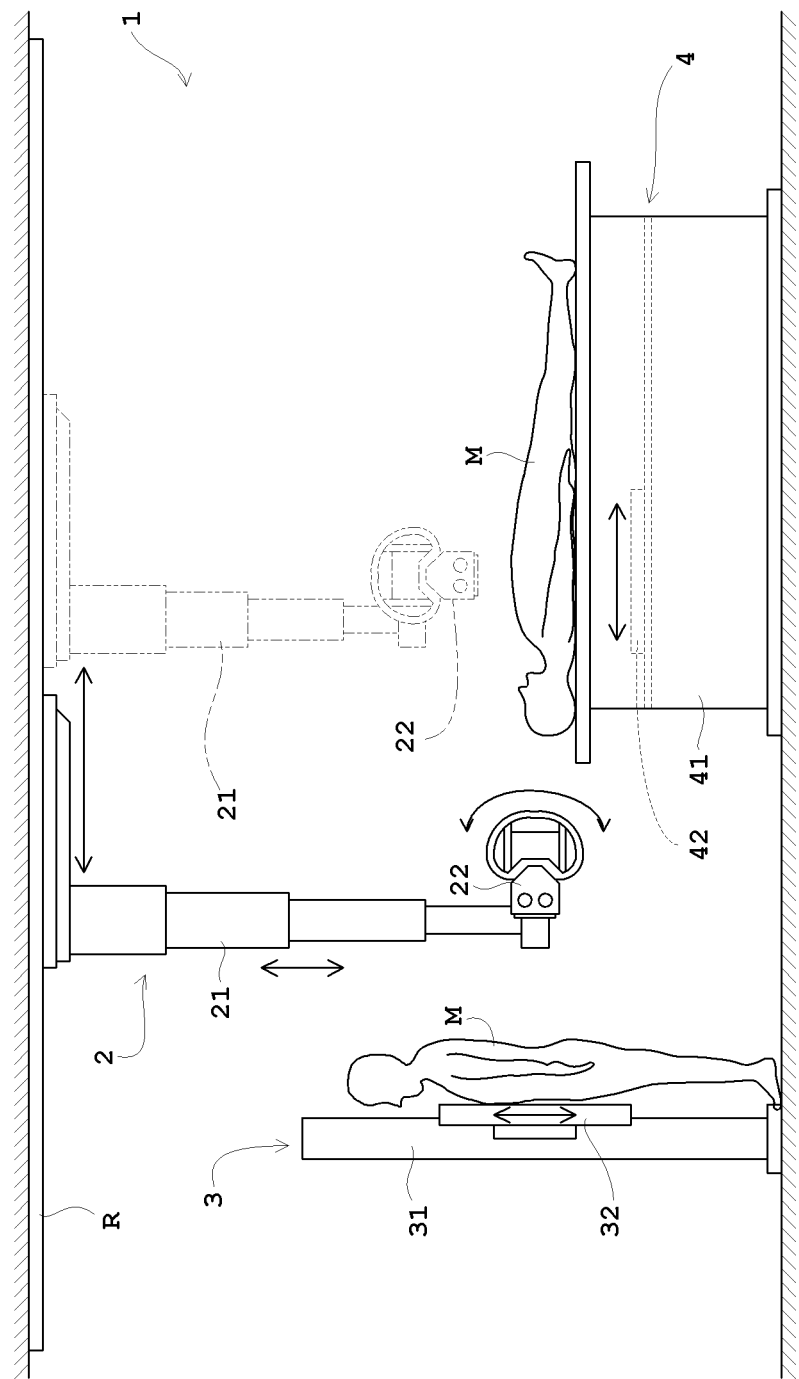
FIG. 1 is a schematic view of an X-ray apparatus according to an example.

6 . . . X-ray image processor
22 . . . X-ray tube
22a . . . collimator (X-ray collimator)
28, 36, 46 . . . controller
29 . . . line marker
29a . . . halogen lamp
29b . . . LED (light emitting diode)
32, 42 . . . flat-panel X-ray detector (FPD)
L . . . imaging area
A . . . upper edge position
B . . . lower edge position

EXAMPLES

Figure 2:
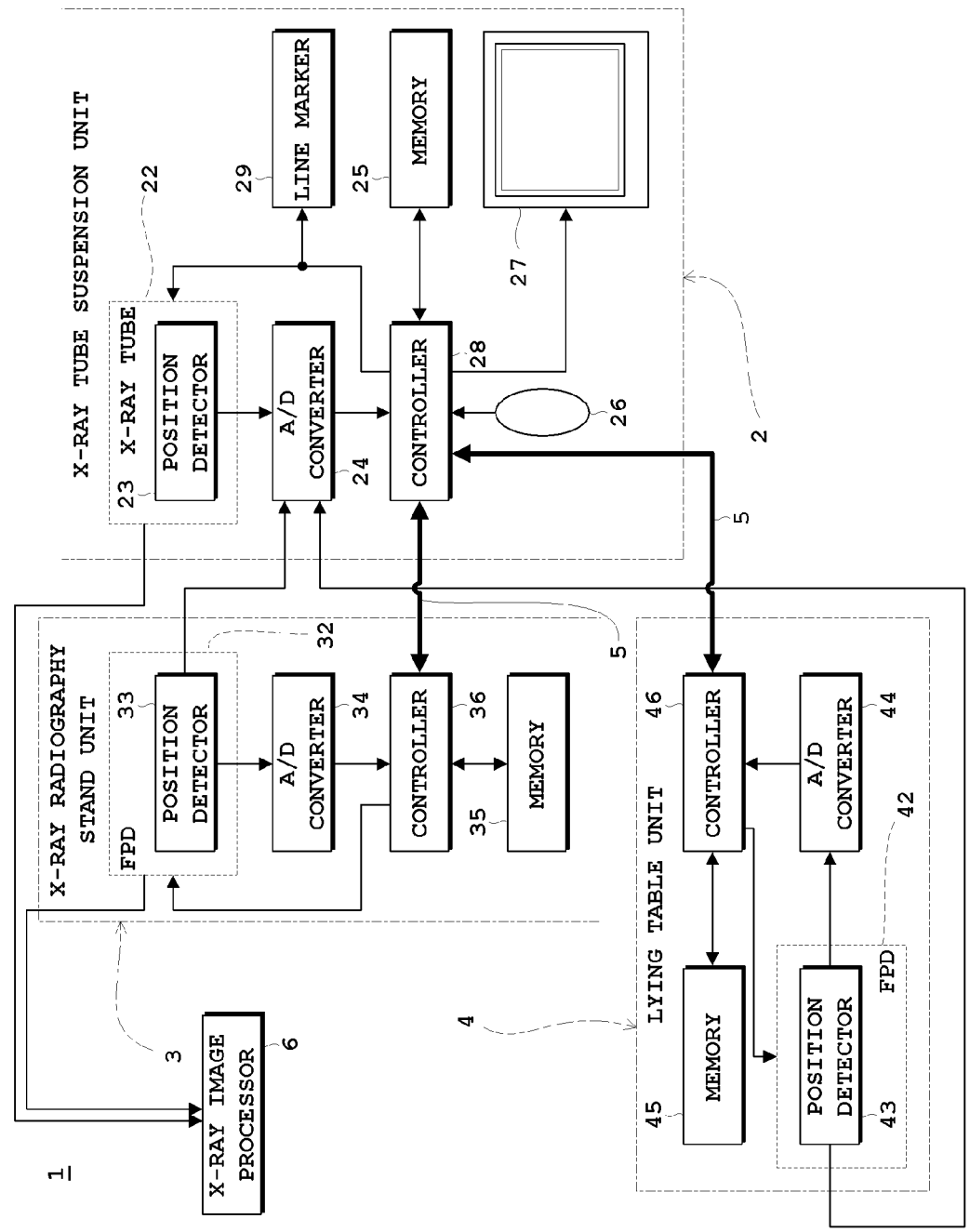
FIG. 2 is a block diagram of the X-ray apparatus according to the example.
Figure 3:
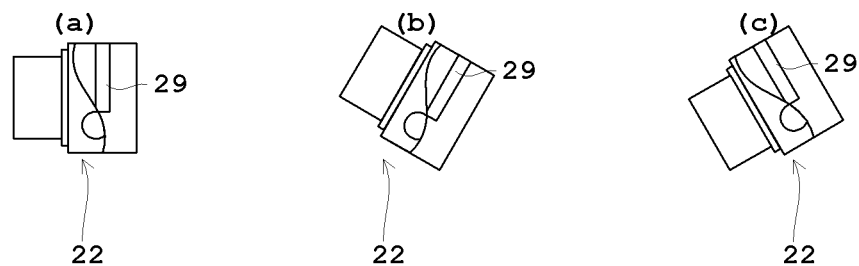
FIGS. 3(a) through 3(c) are schematic views each showing a line marker provided in an X-ray tube.

One example of this invention is to be described in detail hereinafter with reference to the drawings. FIG. 1 is a schematic view of an X-ray apparatus according to an example. FIG. 2 is a block diagram of the X-ray apparatus according to the example. FIG. 3 is a schematic view each showing a line marker provided in an X-ray tube. This example will be described by taking a flat panel X-ray detector (FPD: Flat Panel Detector) as one example of the X-ray detecting device, and a line marker as one example of the light illuminating device.

As shown in FIG. 1, an X-ray apparatus according to this example of the invention includes an X-ray tube suspension unit 2 that suspends an X-ray tube 22 such that the X-ray tube 22 moves along a ceiling, an X-ray radiography stand unit 3 for conducting imaging of a subject M in a standing posture, and a lying table unit 4 for performing radiography for the subject M in a lying posture. As shown in FIG. 2, the X-ray tube suspension unit 2, the X-ray radiography stand unit 3, and the lying table unit 4 are electrically connected to one another via a telecommunication cable 5, through which the X-ray tube suspension unit 2, the X-ray radiography stand unit 3, and the lying table unit 4 can be communicated with one another.

As shown in FIG. 2, the X-ray apparatus 1 according to this example of the invention further includes an X-ray image processor 6. Flat-panel X-ray detectors (FPD) 32 and 42 to be mentioned later detect and obtain two or more X-ray images. The X-ray images are sent to the X-ray image processor 6, where the two or more X-ray images are combined. The X-ray image processor 6 corresponds to the image combining device in this invention.

As shown in FIG. 1, the X-ray tube suspension unit 2 includes a strut 21 that can move along the ceiling and can expand upward and downward, and an X-ray tube 22 that is supported by the strut 21. A direction of the X-ray tube 22 is adjustable. As shown in FIG. 2, the X-ray tube suspension unit 2 also includes a position detector 23 for detecting a position and an angle of the X-ray tube 22, and an A/D converter 24 for converting analog voltage as positional information into digital data, the analog voltage being obtained by the position detector 23 and position detectors 33 and 43 to be mentioned later. The X-ray tube suspension unit 2 further includes a memory 25, an input unit 26, an output unit 27, and a controller 28. Here, the X-ray tube 22 corresponds to the X-ray irradiating device in this invention.

As shown in FIG. 1, the X-ray radiography stand unit 3 includes an erect stand 31 for supporting the subject M placed thereon in a standing posture and a flat-panel X-ray detector (FPD) 32 that is installed on the erect stand 31 and can move upward and downward. As shown in FIG. 2, the X-ray radiography stand unit 3 also includes a position detector 33 for detecting a position of the FPD 32, an A/D converter 34 for converting analog voltage as positional information into digital data, the analog voltage being obtained by the position detector 33. The X-ray radiography stand unit 3 further includes a memory 35, and a controller 36. Similar to the X-ray tube suspension unit 2, the X-ray radiography stand unit 3 may include an input unit and an output unit. Alternatively, the X-ray radiography stand unit 3 does not include the memory 35 and the controller 36, but the controller 28 of the X-ray tube suspension unit 2 directly controls the FPD 32 of the X-ray radiography stand unit 3, or the like. Such configuration may be adopted. Here, the FPD 32 of the X-ray radiography stand unit 3, and an FPD 42 of a lying table unit 4 to be mentioned later correspond to the X-ray detecting device in this invention.

As shown in FIG. 1, the lying table unit 4 includes a lying table 41 for supporting the subject M placed thereon in a lying posture, and a flat-panel X-ray detector (FPD) 42 that is installed on the lying table 41 and can move horizontally. As shown in FIG. 2, the lying table unit 4 also includes a position detector 43 for detecting a position of the FPD 42, and an A/D converter 44 for converting analog voltage as positional information into digital data, the analog voltage being obtained by the position detector 43. The lying table unit 4 further includes a memory 45, and a controller 46. Similar to the X-ray tube suspension unit 2, the lying table unit 4 may include an input unit and an output unit. Alternatively, the lying table unit 4 does not include the memory 45 and the controller 46, but the controller 28 of the X-ray tube suspension unit 2 directly controls the FPD 42 of the lying table unit 4, or the like. Such configuration may be adopted.

The strut 21 of the X-ray tube suspension unit 2 can move along a rail R provided on the ceiling. The rail R is also provided in a direction perpendicular to the plane of FIG. 1. Thus, the strut 21 can also move in the direction perpendicular to the plane. The strut 21 can expand upward and downward, and supports the X-ray tube 22. Thus the X-ray tube 22 can move horizontally/vertically. Moreover, a direction of the X-ray tube 22 is adjustable. As a result, the direction of the X-ray tube 22 is adjusted through horizontal/vertical movement of the X-ray tube 22 toward the erect stand 31 of the X-ray radiography stand unit 3 as shown by solid lines in FIG. 1, whereby X-ray radiography can be conducted in the standing posture. Alternatively, the direction of the X-ray tube 22 is adjusted through horizontal/vertical movement of the X-ray tube 22 toward the lying table 41 of the lying table unit 4 as shown by two-dot chain lines in FIG. 1, whereby X-ray radiography can be conducted in the lying posture.

As shown in FIG. 2, the position detector 23 is provided in the X-ray tube 22. The position detector 23 detects a position and an angle of the X-ray tube 22. For instance, the position detector 23 is composed of a potentiometer. Resistance of the potentiometer varies as the X-ray tube 22 moves or rotates, and output voltage varies relative to reference voltage as the resistance varies. The output voltage is analog voltage. The analog voltage as positional information (also including an angle) obtained by the potentiometer is sent into the A/D converter 24 where the analog voltage is converted into digital data.

The memory 25 of the X-ray tube suspension unit 2 writes in and stores the area, set in advance, capable of being imaged via the controller 28, and reads it out appropriately as required. The memory 25 of the X-ray tube suspension unit 2, the memory 35 of the X-ray radiography stand unit 3 and the memory 45 of the lying table unit 4 each have a storage medium, typically a ROM (Read-Only Memory) or RAM (Random Access Memory).

The input unit 26 of the X-ray tube suspension unit 2 sends into the controller 28 data and commands inputted by an operator. The input unit 26 is formed of a pointing device represented by such as a mouse, keyboard, joystick, trackball, and touch panel. In this example, depressing a positioning button (an upper edge positioning button and a lower edge positioning button) determines the upper edge position and lower edge position at that time, whereby an imaging area is determined.

The output unit 27 of the X-ray tube suspension unit 2 is composed of a display screen, a printer, or the like, the display screen being represented by a monitor, and a printer. In this example, the output unit 27 is formed by a touch panel equipped with the aforementioned positioning button of the input unit 26. The touch panel is attached to the X-ray tube 22. Thus, the output unit 27 may have the function of the input unit 26.

The controller 28 of the X-ray tube suspension unit 2 controls each section en block that forms the X-ray tube suspension unit 2. The controller 28 of the X-ray tube suspension unit 2, the controller 36 of the X-ray radiography stand unit 3, and the controller 46 of the lying table unit 4 each has a central processing unit (CPU) and the like. In this example, the controller 28 has an edge determination function that determines the edge of the imaging area of the image combined by long-length imaging through light illumination by the line marker 29 (see FIGS. 2 and 3) to be mentioned later and a control function that performs control such that light from the line marker 29 is not emitted outside beyond the area, set in advance, capable of being imaged. Where the output unit 27 is a display screen, output display is performed. Where the output unit 27 is a printer, output printing is performed. Here, the controller 28 of the X-ray tube suspension unit 2 corresponds to the edge determination device and the control device in this invention.

In addition, as shown in FIG. 3, the X-ray tube 22 is provided with the line marker 29 as the illumination device. Laser is used for the line marker 29. As the direction of the X-ray tube 22 is adjusted and inclines from the state in FIG. 3(a) to the state in FIG. 3(b) or 3(c), the line marker 29 also inclines accordingly. The line marker 29 has an advantage that light from the line marker 29 does not get blurred readily, and thus can be recognized as a profile view of light in a line state. Of course, the illumination device is not limited to the line marker 29. It is not particularly limited when it is the light illuminating device used in usual such as a halogen lamp or an LED (light emitting diode). Here, the line marker 29 corresponds to the light illuminating device in this invention.

As shown in FIG. 1, the erect stand 31 of the X-ray radiography stand unit 3 is set to the floor. The FPD 32 of the X-ray radiography stand unit 3 can move upward and downward along the erect stand 31. Moreover, the lying table 41 of the lying table unit 4 is also set to the floor. The FPD 42 of the lying table unit 4 can move horizontally within the lying table 41.

As shown in FIG. 2, the position detector 33 is provided in the FPD 32 of the X-ray radiography stand unit 3. The position detector 33 detects the position of the FPD 32. Moreover, the position detector 43 is also provided in the FPD 42 of the lying table unit 4. The position detector 43 detects the position of FPD 42. Similar to the position detector 23 of the X-ray tube suspension unit 2, the position detector 33 of the X-ray radiography stand unit 3 or the position detector 43 of the lying table unit 4 is composed of a potentiometer. Resistance of the potentiometer varies as the FPDs 32 and 42 move, and output voltage varies relative to reference voltage as the resistance varies. The output voltage is analog voltage. The analog voltage as positional information obtained by the potentiometer is sent into the A/D converter 34 of the X-ray radiography stand unit 3 and the A/D converter 44 of the lying table unit 4. In the A/D converters 33 and 44, the analog voltage is converted into digital data. Moreover, the analog voltage as positional information obtained by the potentiometer of the X-ray radiography stand unit 3 or the lying table unit 4 is also sent into the A/D converter 24 of the X-ray tube suspension unit 2.

The memory 35 of the X-ray radiography stand unit 3 writes in and stores the area, set in advance, capable of being imaged via the controller 36, and reads it out appropriately as required. The memory 45 of the lying table unit 4 writes in and stores the area, set in advance, capable of being imaged via the controller 46, and reads it out appropriately as required.

The controller 36 of the X-ray radiography stand unit 3 controls each section en block that forms the X-ray radiography stand unit 3. The controller 46 of the lying table unit 4 controls each section en block that forms the lying table unit 4.

The controller 28 of the X-ray tube suspension unit 2 and the controller 36 of the X-ray radiography stand unit 3 are electrically connected to each other via the telecommunication cable 5. The controller 28 of the X-ray tube suspension unit 2 and the controller 46 of the lying table unit 4 are electrically connected to each other via the telecommunication cable 5. Such connection can cause the X-ray tube suspension unit 2, the X-ray radiography stand unit 3, and the lying table unit 4 to be communicated with one another. Moreover, the controllers 28, 36, and 46 control drive of the X-ray tube 22, and the FPDs 32, 42, respectively. The controllers 28, 36, and 46 control a motor, not shown, thereby driving by motor the X-ray tube 22 and the FPDs 32, 42. Such motor driving can cause the X-ray tube 22 or the FPDs 32, 42 to be controlled in a desired position and can cause the direction of the X-ray tube 22 to be adjusted at a desired angle.

Figure 8:
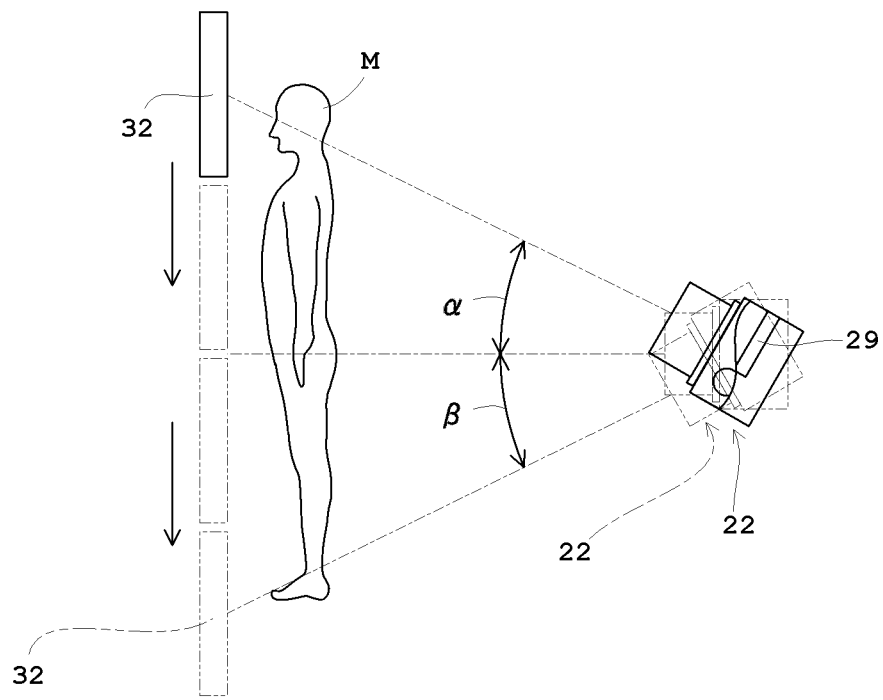
FIG. 8 is a schematic view of long-length imaging after the determination of the imaging area.

In the long-length imaging, as shown in FIG. 8 to be mentioned later, the controller 28 of the X-ray tube suspension unit 2 control the X-ray tube 22 to emit X-rays continuously while driving the X-ray tube 22 by motor such that the direction of the X-ray tube 22 is adjusted and inclined. The controller 36 of the X-ray radiography stand unit 3 drives the FPD 32 by motor to move it upward and downward.

Figure 4:
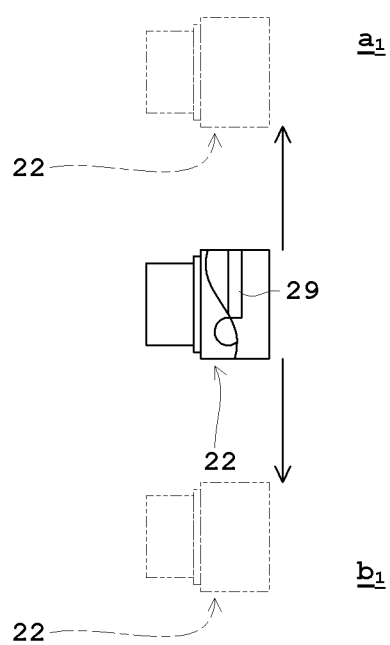
FIG. 4 is a schematic view when an area capable of being imaged is set in accordance with a movable area of the X-ray tube.
Figure 5:
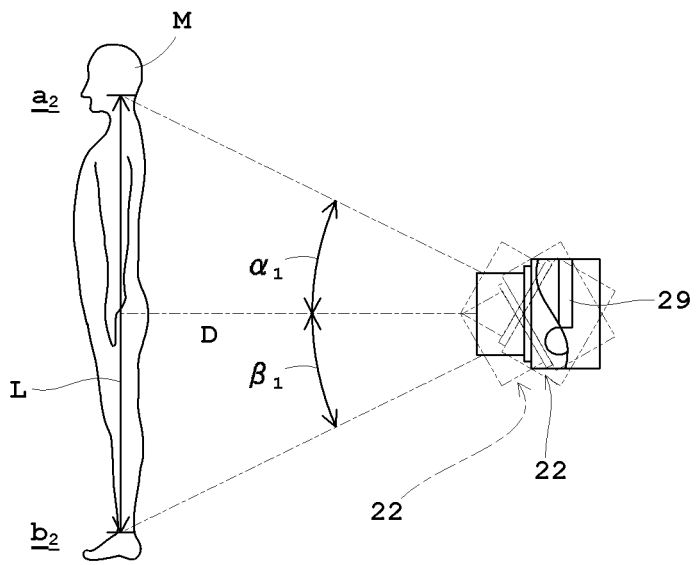
FIG. 5 is a schematic view when the area capable of being imaged is set in accordance with an exposure area of the X-ray tube.
Figure 6:
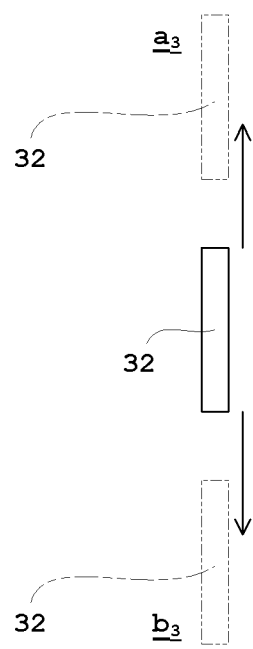
FIG. 6 is a schematic view when the area capable of being imaged is set in accordance with a movable area of a flat-panel X-ray detector (FPD).
Figure 7:
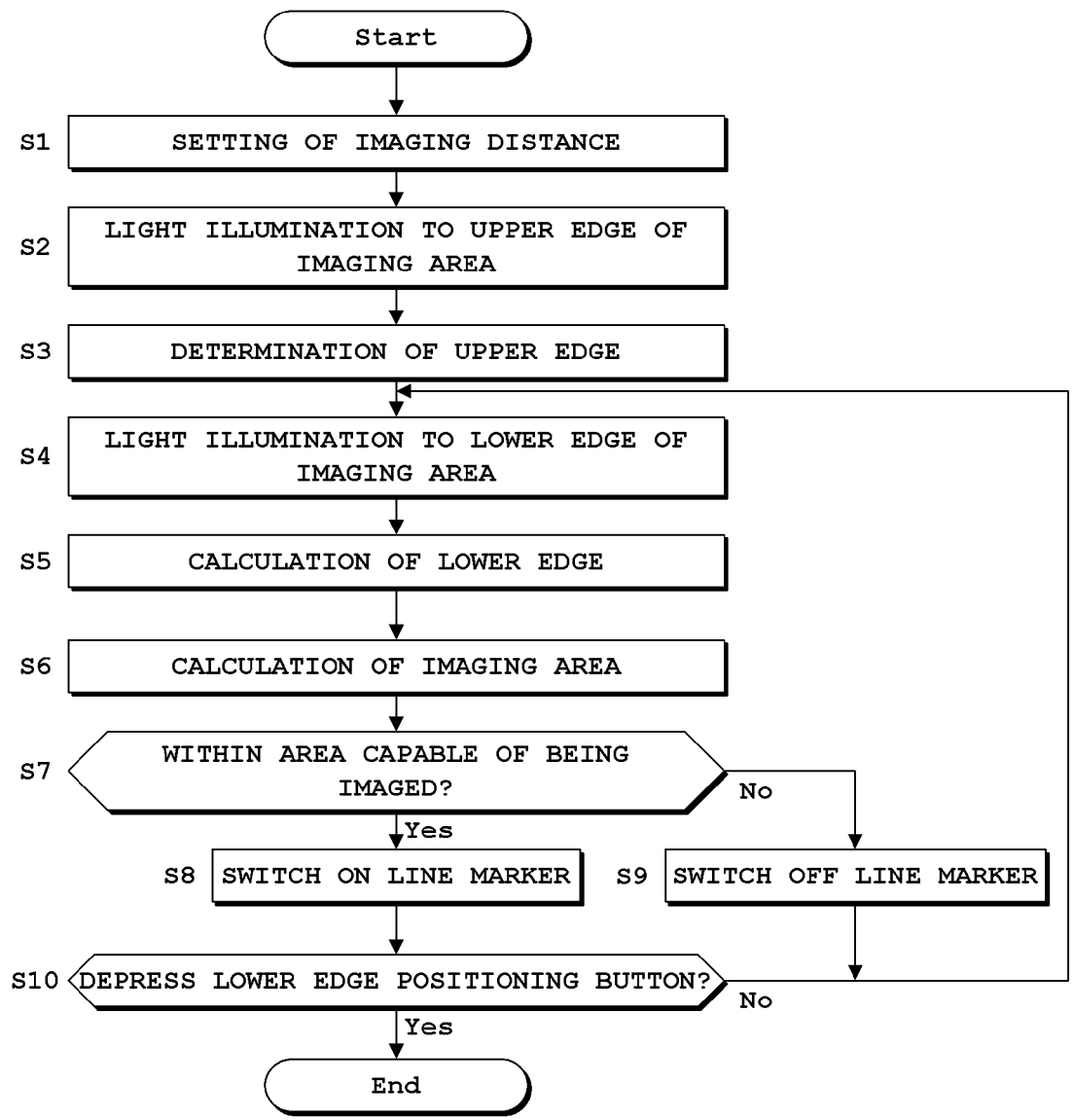
FIG. 7 is a flow chart showing determination of an imaging area through a series of light illumination.
Figure 9:
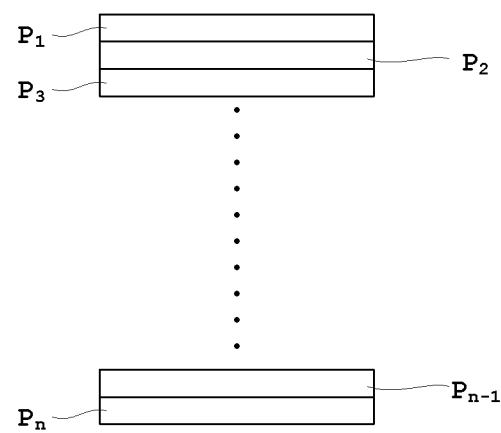
FIG. 9 is a schematic view upon combining a plurality of X-ray images in the long-length imaging.

Subsequently, descriptions will be given of setting of the area capable of being imaged, determination of the imaging area through a series of light illumination and long-length imaging after the determination with reference to FIGS. 4 through 9. FIG. 4 is a schematic view when an area capable of being imaged is set in accordance with a movable area of the X-ray tube. FIG. 5 is a schematic view when an area capable of being imaged is set in accordance with an exposure area of the X-ray tube. FIG. 6 is a schematic view when an area capable of being imaged is set in accordance with a movable area of a flat-panel X-ray detector (FPD). FIG. 7 is a flow chart showing determination of an imaging area through a series of light illumination. FIG. 8 is a schematic view of long-length imaging after the determination of the imaging area. FIG. 9 is a schematic view upon combining a plurality of X-ray images in the long-length imaging. FIGS. 4 through 9 have been described by taking the case as one example where the FPD 32 is moved upward and downward along the erect stand 31.

For setting in advance the area capable of being imaged, as shown in FIG. 4 for example, an upper bound $a_1$ and a lower bound $b_1$ of the X-ray tube 22 are written and stored as a movable area of the X-ray tube 22 into the memory 25 of the X-ray tube suspension unit 2. The upper bound $a_1$ and the lower bound $b_1$ is limited by stroke of the strut 21 (not shown in FIG. 4.)

Moreover, for setting in advance the area capable of being imaged, as shown in FIG. 5 for example, maximum angles $\alpha_1$ and $\beta_1$ within an inclination area of the X-ray tube 22 are written and stored as an exposure area of the X-ray tube 22 into the memory 25 of the X-ray tube suspension unit 2. Here, upon setting in advance the area capable of being imaged in accordance with the exposure area of the X-ray tube 22 as shown in FIG. 5, an upper exposure bound $a_2$ and a lower exposure bound $b_2$ of the X-ray tube 22 vary depending on the imaging distance D between the subject M and the X-ray tube 22 and the focusing position of the X-ray tube 22. Thus the area capable of being imaged is set in advance for every imaging distance D and every focusing position of the X-ray tube 22 and then is written and stored into the memory 25. Such configuration may be adopted.

Furthermore, for setting in advance the area capable of being imaged, as shown in FIG. 6 for example, an upper bound $a_3$ and a lower bound $b_3$ of the FPD 32 are written and stored as a movable area of the FPD 32 into the memory 35 of the X-ray radiography stand unit 3. The upper bound $a_3$ and the lower bound $b_3$ are limited by stroke of the erect stand 31 (not shown in FIG. 6.) Here, the movable area of the FPD 32 is not written into the memory 35, but may be written into the memory 25 of the X-ray tube suspension unit 2 via the controller 36 of the X-ray radiography stand unit 3 or the controller 28 of the X-ray tube suspension unit 2. Alternatively, the movable area of the FPD 32 may be written and stored directly into the memory 25 of the X-ray tube suspension unit 2. For also backup, the movable area of the FPD 32 may be written and stored into the memory 35 of the X-ray radiography stand unit 3, and may also be written and stored into the memory 25 of the X-ray tube suspension unit 2.

Setting in advance the area capable of being imaged is completed, and then a flow illustrated in FIG. 7 is performed. Here, it is assumed that the upper edge position represented by "A" in FIG. 7 is below the upper bound $a_1$ of the X-ray tube 22 in FIG. 4, the exposure bound $a_2$ of the X-ray tube 22 in FIG. 5, and the upper bound $a_3$ of the FPD 32 in FIG. 6, and light from the line marker 29 is continuously switched on. Description hereunder will be given under this assumption. In FIG. 7, the FPD 32 does not always need to move. Moreover, the X-ray tube 22 does not need to actually emit X-rays, but the line marker 29 only needs to emit lights.

(Step S1) Setting of Imaging Distance

The X-ray tube 22 is moved to an imaging position in long-length imaging, and then an imaging distance D is set.

(Step S2) Light Illumination to Upper Edge of Imaging Area

The X-ray tube 22 is inclined upward while a focusing position is fixed in a position where the imaging distance D is set, whereby the line marker 29 is also inclined upward. Light is illuminated from the line marker 29 toward the upper edge of the imaging area.

(Step S3) Determination of Upper Edge

Then an upper edge positioning button is depressed. The controller 28 determines the upper edge position A in accordance with the angle $\alpha$ and the imaging distance D of the X-ray tube 22 at this time.

(Step S4) Light Illumination to Lower Edge of Imaging Area

The X-ray tube 22 is inclined downward, whereby the line marker 29 is also inclined downward. Light is illuminated from the line marker 29 toward the lower edge of the imaging area.

(Step S5) Calculation of Lower Edge

The controller 28 determines a lower edge position represented by "B" in accordance with the angle $\beta$ and the imaging distance D of the X-ray tube 22 at this time.

(Step S6) Calculation of Imaging Area

The controller 28 determines an imaging area L in accordance with the upper edge position A determined in Step S3 and the lower edge position B determined in Step S5. Then the controller 28 determines the lower edge of the FPD 32 for X-rays entering from the X-ray tube 22. Here, the lower edge of the FPD 32 can be determined without actually moving the FPD 32.

(Step S7) Within Area Capable of being Imaged?

The controller 28 determines whether or not the focusing position of the X-ray tube 22, the exposure area of the X-ray tube 22 at the angles α and β, the upper edge position A determined in Step S3, the lower edge position B determined in Step S5, and the imaging area L, and the lower edge of the FPD 32 determined in Step S6 are within the area, set in advance, capable of being imaged. Specifically, it is assumed that they are within the area capable of being imaged when the focusing position of the X-ray tube 22 is between the upper bound $a_1$ and the lower bound $b_1$ of the X-ray tube 22 shown in FIG. 4, the exposure area of the X-ray tube 22 at the angles α and β is between the maximum angles $α_1$ and $β_1$ shown in FIG. 5, the upper and lower edge positions A and B of the X-ray tube 22 are between the upper exposure bound $a_2$ and the lower exposure bound $b_2$ of the X-ray tube 22, and the lower edge of the FPD 32 is above the lower bound $b_3$ shown in FIG. 6. Where they are within the area capable of being imaged, the process proceeds to Step S8. Where they are not within the area capable of being imaged, i.e., they are beyond the area, set in advance, capable of being imaged, the process proceeds to Step S9.

(Step S8) Switch on Line Marker

Where they are within the area capable of being imaged, the controller 28 continuously switches the line marker 29 on, and the process proceed to Step S10.

(Step S9) Switch Off Line Marker

Where they are not within the area capable of being imaged, the controller 28 performs control such that line marker 29 is switched off, and the process returns to Step S4. Then the controller 28 inclines the X-ray tube 22 and the line marker 29 at another position, and Steps S4 through S7 are repeated until they are within the area capable of being imaged.

(Step S10) Depress Lower Edge Positioning Button?

When they are within the area capable of being imaged but are not in the desired lower edge, the lower-edge positioning button is not depressed and the process returns to Step S4. Then the controller 28 inclines the X-ray tube 22 and the line marker 29 at another position, and Steps S4 through S7 are repeated until they are in the desired lower edge position and within the area capable of being imaged. When they are in the desired lower edge position and within the area capable of being imaged, the lower-edge positioning button is depressed.

The Steps S1 through S10 are performed, whereby the controller 28 determines the edge of the imaging area of the image (the lower edge B in the flow of FIG. 7) combined by long-length imaging.

Next, where the actual long imaging is performed after the determination as above, the X-ray tube 22 emits X-rays while being inclined, and the FPD 32 is moved such that X-rays enter thereinto. Here, it is not always necessary to apply light from the line marker 29 in the long-length imaging. In this example, the controller 28 performs control such that the X-ray tube 22 continuously emits X-rays in the imaging area determined in the Steps S1 through S10 while driving by motor the X-ray tube 22 to continuously incline the X-ray tube 22 with the direction thereof being adjusted. Then the controller 28 sends commands to the controller 36 of the X-ray radiography stand unit 3 via the telecommunication cable 5. The controller 36 drives by motor the FPD 32 to move the FPD 32 upward and downward (In FIG. 8, move the FPD 32 downward) such that X-rays from the inclined X-ray tube 22 enter into the FPD 32.

Returning to the description of FIG. 1, the X-ray image processor 6 in this example obtains X-ray images based on X-rays detected for every exposure in the FPD 32. The two or more X-ray images are combined in the movement direction of the FPD 32 and in the inclination direction of the X-ray tube 22, whereby a long image can be acquired.

Specifically, the X-ray images obtained for every exposure within the imaging area determined in the Steps S1 through S10 are assumed as $P_1, P_2, P_3, \ldots, P_{n-1}, P_n$, in order, as shown in FIG. 9. X-ray images $P_1$ and $P_2$ adjacent to each other are connected and combined in the movement direction of the FPD 32 and the inclination direction of the X-ray tube 22, and a next adjacent X-ray image $P_3$ is connected to and combined with the combined X-ray image in the movement direction of the FPD 32 and the inclination direction of the X-ray tube 22. Such process is repeated until obtaining an X-ray image $P_n$. That is, the X-ray images adjacent to each other are connected to and combined with each other in the movement direction of the FPD 32 and the inclination direction of the X-ray tube 22.

The specification has a description that the direction of the X-ray tube 22 is adjusted through horizontal/vertical movement of the X-ray tube 22 toward the erect stand 31 of the X-ray radiography stand unit 3 as shown by solid lines in FIG. 1, whereby the area capable of being imaged for conducting long-length imaging in the standing posture can be determined, and the imaging area can be determined through a series of light illumination. Moreover, the specification has a description of long-length imaging in the standing posture after the determination as above. Except for the lying posture in the horizontal direction instead of the standing posture in the vertical direction as in FIG. 8, the same procedure can be made to the determination of the area capable of being imaged for long-length imaging in the lying posture by adjusting the direction of the X-ray tube 22 through horizontal/vertical movement of the X-ray tube 22 toward the lying table 41 of the lying table unit 4 as shown by two-dot chain lines in FIG. 1 and the determination of the area capable of being imaged through a series of light illumination as well as long-length imaging in the lying posture after the determination as above.

According to the X-ray apparatus 1 with the aforementioned configuration in this example, the controller 28 determines, using the edge determination function, the edge of the imaging area of the image (the lower edge B in the flow of FIG. 7) combined by the X-ray image processing device with the image combination function through light illumination from the line marker 29. Thereby the controller 28 performs control such that light from the line marker 29 is not emitted outside beyond the area, set in advance, capable of being imaged. Consequently, an operator just performs operation while looking at only light from the line marker 29 upon determination of the imaging area, which achieves easy operation. As a result, operation upon determination of the imaging area can be facilitated.

The aforementioned area, set in advance, area capable of being imaged is determined in accordance with the movable area of the X-ray tube 22 as in FIG. 4, the exposure area of the X-ray tube as in FIG. 5, or the movable area of the flat-panel X-ray detector (FPD) 32 in FIG. 6. The area capable of being imaged may be set in accordance with such mechanical restrictions, and may be used for control of the line marker 29.

In this example, control such that light from the line marker 29 is not emitted outside beyond the area, set in advance, area capable of being imaged may be achieved through switching off the line marker 29.

This invention is not limited to the foregoing embodiment, but may be modified as follows.

(1) The foregoing example has an X-ray apparatus 1 as shown in FIG. 1. The apparatus may be an apparatus for long-length imaging only in the standing posture or only in the lying posture as long as the apparatus for long-length imaging combines two or more X-ray images. Alternatively, the apparatus for long-length imaging may be adopted having a table that can be inclined and is applicable for both standing posture and the lying posture.

Figure 10:
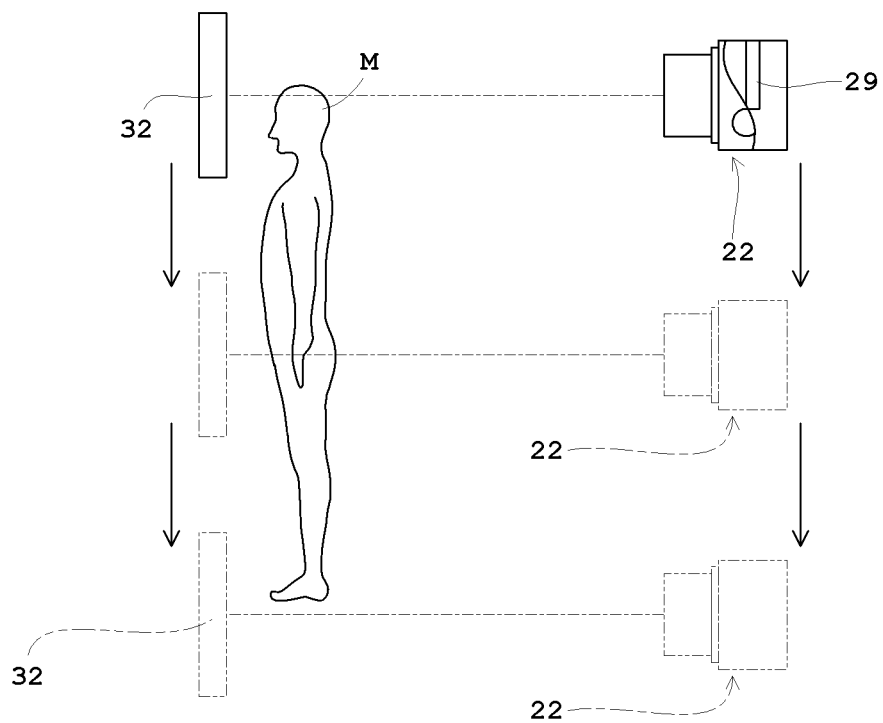
FIG. 10 is a schematic view of long-length imaging after determination of an imaging area according to one modification.

(2) In the foregoing example, long-length imaging is performed through moving the flat-panel X-ray detector (FPD) 32 while the X-ray tube 22 is inclined as shown in FIG. 8. Alternatively, as shown in FIG. 10, long-length imaging may be performed through moving the FPD 32 while the X-ray tube 22 is also moved. Moreover, long-length imaging may be performed through moving a table for supporting the subject M placed thereon while the X-ray tube and the FPD are affixed. Furthermore, long-length imaging may be performed through moving a table for supporting the subject M placed thereon while the X-ray tube and the FPD are also moved.

(3) In the foregoing example, only the lower edge is determined for determination of the edge of the imaging area. Alternatively, the upper edge may also be determined, or only the upper edge may be determined. At this time, control is made such that the light illuminating device (the line marker 29 in the example) is switched off when the light illuminating device applies light over the upper edge beyond the area capable of being imaged. Similar to the imaging in the horizontal direction, one end of the imaging area may be determined or both ends thereof may be determined.

Figure 11:
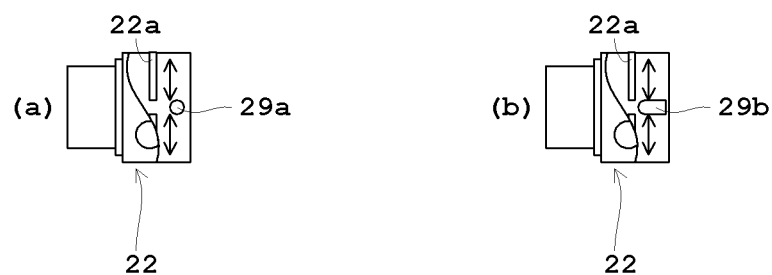
FIG. 11(a) is a schematic view when a halogen lamp is provided in the X-ray tube.
FIG. 11(b) is a schematic view when an LED is provided in the X-ray tube.
Figure 12:
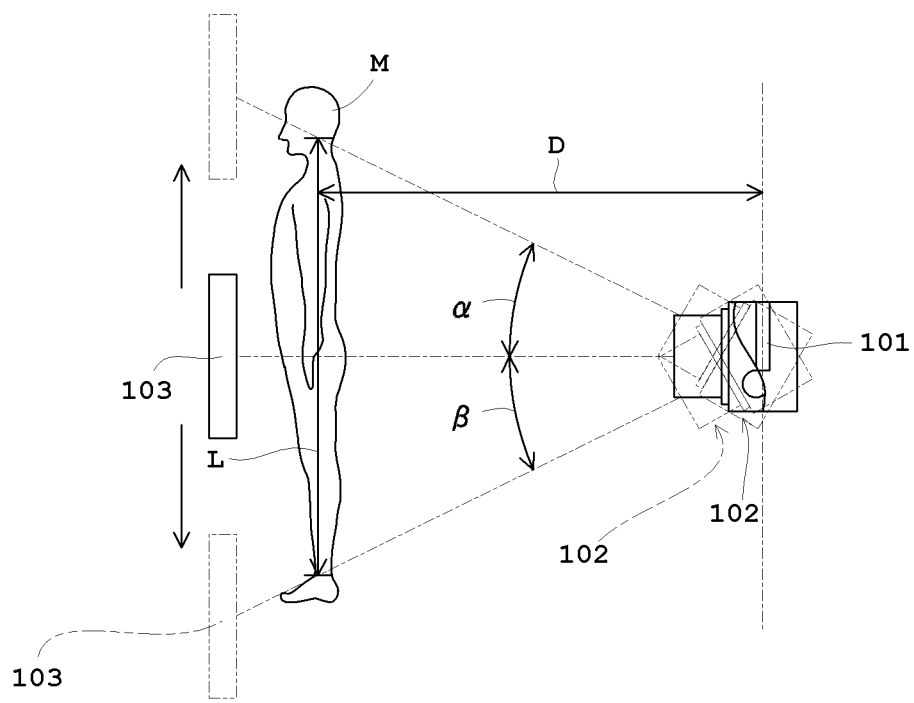
FIG. 12 is a schematic view of an approach when the imaging area is determined in the long-length imaging.

(4) In the foregoing example, control such that light from the light illuminating device (the line marker 29 in the example) is not emitted outside beyond the area, set in advance, capable of being imaged may be achieved through switching off the light illuminating device (the line marker 29). Alternatively, this may be achieved through intercepting light by an intercepting device provided for intercepting light from the light illuminating device. For instance, when the halogen lamp 29*a* as shown in FIG. 11(*a*) or the LED (light emitting diode) 29*b* as shown in FIG. 11(*b*) is used for the light illuminating device, and the collimator (X-ray collimator) 22*a* for controlling a field of view of the X-ray from the X-ray tube 22 is used for the intercepting device, the collimator 22*a* may intercept light beyond the area, set in advance, capable of being imaged. In FIGS. 11(*a*) and 11(*b*), the collimator 22*a* is used for control of the field of view and light interception. Alternatively, another intercepting device other than the collimator 22*a* may be used for light interception only. Here, the collimator 22*a* corresponds to the intercepting device in this invention. The halogen lamp 29*a* and the LED 29*b* correspond to the light illuminating device in this invention.

(5) The foregoing example has been described by taking the flat-panel X-ray detector as an example of the X-ray detecting device. The X-ray detecting device is not particularly limited as long as it is used in ordinary circumstances such as an image intensifier (I.I).

The invention claimed is:

1. An X-ray apparatus for conducting X-ray radiography, comprising:
    an X-ray irradiating device for irradiating a subject with X-rays;
    an X-ray detecting device for detecting X-rays transmitting through the subject;
    an image combining device for combining two or more X-ray images;
    a light illuminating device for illuminating the subject;
    an edge determining device for determining an edge of an imaging area of an image combined by the image combining device based on the illumination by the light illuminating device; and
    a control device for performing control such that light from the light illuminating device is not emitted outside beyond a possible imaging area, set in advance, when the edge of the imaging area determined by the edge determining device is beyond the possible imaging area.

2. The X-ray apparatus according to claim 1, wherein the possible imaging area is set in accordance with a movable area of the X-ray irradiating device.

3. The X-ray apparatus according to claim 1, wherein the possible imaging area is set in accordance with an exposure area of the X-ray irradiating device.

4. The X-ray apparatus according to claim 1, wherein the possible imaging area is set in accordance with a movable area of the X-ray detecting device.

5. The X-ray apparatus according to claim 1, wherein the control device performs control such that the light illuminating device is switched off when the light illuminating device illuminates the area outside the possible imaging area.

6. The X-ray apparatus according to claim 1, further comprising:
    an intercepting device for intercepting light from the light illuminating device, wherein
    the control device performs control such that the intercepting device intercepts the light when the light illuminating device illuminates the area outside the possible imaging area.

7. The X-ray apparatus according to claim 6, wherein the intercepting device is a collimator for controlling a field of view of X-rays from the X-ray irradiating device.

8. The X-ray apparatus according to claim 6, further comprising:
    a collimator for controlling a field of view of X-rays from the X-ray irradiating device, wherein
    the intercepting device is only used for intercepting light.

9. The X-ray apparatus according to claim 1, wherein the light illuminating device is a line marker.

10. The X-ray apparatus according to claim 1, wherein the light illuminating device is a halogen lamp.

11. The X-ray apparatus according to claim 10, further comprising an intercepting device for intercepting light from the halogen lamp, wherein
    the control device performs control such that the intercepting device intercepts the light when the light illuminating device illuminates the area outside the possible imaging area.

12. The X-ray apparatus according to claim 1, wherein the light illuminating device is an LED.

13. The X-ray apparatus according to claim 12, further comprising an intercepting device for intercepting light from the LED, wherein
    the control device performs control such that the intercepting device intercepts the light when the light illuminating device illuminates the area outside the possible imaging area.

14. The X-ray apparatus according to claim 1, wherein the edge determining device determines one end of the imaging area.

15. The X-ray apparatus according to claim 1, wherein the edge determining device determines both ends of the imaging area.

16. The X-ray apparatus according to claim 1, wherein X-ray radiography is conducted for the subject in a standing posture.

17. The X-ray apparatus according to claim 1, wherein X-ray radiography is conducted for the subject n a lying posture.

18. The X-ray apparatus according to claim 1, wherein X-ray radiography is conducted for the subject in a standing posture and in a lying posture.

19. The X-ray apparatus according to claim 1, wherein the control device is configured to:
   determine whether the light illuminating device illuminates an area outside a possible imaging area within which the two or more X-ray images are obtained, and
   stop the illumination by the light illumining device when the light illuminating device illuminates the area outside the possible imaging area.

20. The X-ray apparatus according to claim 1, wherein one or more processors are configured to perform as the image combining device, the edge determining device, and the control device.

* * * * *